(12) United States Patent
Kim et al.

(10) Patent No.: US 12,201,351 B2
(45) Date of Patent: Jan. 21, 2025

(54) RF ABLATION CATHETER FOR SEPTAL REDUCTION THERAPY HAVING COOLING EFFECT

(71) Applicant: TAU-PNU MEDICAL CO., LTD., Busan (KR)

(72) Inventors: June Hong Kim, Busan (KR); Kyone Peter Park, Yangsan (KR)

(73) Assignee: TAU MEDICAL INC., Busan (KR)

( * ) Notice: Subject to any disclaimer, the term of this patent is extended or adjusted under 35 U.S.C. 154(b) by 384 days.

(21) Appl. No.: 17/328,482

(22) Filed: May 24, 2021

(65) Prior Publication Data

US 2022/0061915 A1    Mar. 3, 2022

(30) Foreign Application Priority Data

May 22, 2020   (KR) ........................ 10-2020-0061941
Jun. 12, 2020   (KR) ........................ 10-2020-0071558

(51) Int. Cl.
*A61B 18/14*    (2006.01)
*A61B 18/00*    (2006.01)

(52) U.S. Cl.
CPC ...... *A61B 18/1492* (2013.01); *A61B 2018/00029* (2013.01); *A61B 2018/00083* (2013.01);
(Continued)

(58) Field of Classification Search
CPC ...... A61B 18/1492; A61B 2018/00029; A61B 2018/00136; A61B 2018/0038;
(Continued)

(56) References Cited

U.S. PATENT DOCUMENTS

2010/0191151 A1* 7/2010 Kwak ............... A61B 18/1492
                                                              600/585
2015/0073515 A1* 3/2015 Turovskiy .......... A61B 18/1492
                                                              607/101
(Continued)

FOREIGN PATENT DOCUMENTS

JP    2019-103561 A    6/2019
KR    10-1626958          5/2016

OTHER PUBLICATIONS

Liu et al.; Percutaneous Intramyocardial Septal Radiofrequency Ablation for Hypertrophic Obstructive Cardiomyopathy. Journal of the American College of Cardiology vol. 72, Issue 16, Oct. 2018.

*Primary Examiner* — Linda C Dvorak
*Assistant Examiner* — Abigail Bock
(74) *Attorney, Agent, or Firm* — Justin H. Kim (57) ABSTRACT

The present disclosure relates to a RF ablation catheter for septal reduction therapy having a cooling effect, and more particularly, to a RF ablation catheter for septal reduction therapy that is for performing RF ablation, in which RF energy is applied to an interventricular septum, for septal reduction therapy such as therapy for hypertrophic cardiomyopathy, which is a disease in which an interventricular septum of the left ventricle of the heart of the animal or human body thickens, therapy that requires reduction of an interventricular septum, or therapy for ventricular tachycardia. Also, the present disclosure relates to a RF ablation catheter for septal reduction therapy having a cooling effect that is for preventing carbonization of a tissue of the body (interventricular septum) around an electrode.

An exemplary embodiment of the present disclosure provides a RF catheter for septal reduction therapy, the RF catheter including: an intra-septal part in which a tapered tip which becomes thinner toward an end thereof is formed at an end of a distal part and one or more electrodes are formed at positions on an outer circumferential surface that are adjacent to the tip; and a body part which is made of a soft material and has a guidewire lumen which passes through the intra-septal part from an inlet formed at the center of the end of the tip and has an outlet formed in a side surface, a coolant inlet lumen which is connected from a proximal part to an inner portion of the intra-septal part to allow a coolant to be injected from the outside and which has an open end, and a coolant outlet lumen which communicates with the coolant inlet lumen and has an exit formed in a side surface, wherein the guidewire lumen and the coolant inlet lumen do not communicate with each other and are partitioned from each other.

13 Claims, 6 Drawing Sheets

(52) U.S. Cl.
CPC .............. *A61B 2018/00136* (2013.01); *A61B 2018/0038* (2013.01); *A61B 2018/00577* (2013.01); *A61B 2018/00821* (2013.01); *A61B 2018/00839* (2013.01)

(58) Field of Classification Search
CPC ........... A61B 2018/00577; A61B 2018/00821; A61B 2018/00839
See application file for complete search history.

(56) References Cited

U.S. PATENT DOCUMENTS

| | | | | |
|---|---|---|---|---|
| 2017/0348049 A1* | 12/2017 | Vrba | .................. | A61B 18/1492 |
| 2020/0155229 A1* | 5/2020 | Kim | .................. | A61B 18/1492 |
| 2020/0297408 A1* | 9/2020 | Mori | .................. | A61B 18/1477 |

* cited by examiner

FIG. 6

RF ABLATION CATHETER FOR SEPTAL REDUCTION THERAPY HAVING COOLING EFFECT

BACKGROUND

1. Field of the Invention

The present disclosure relates to a RF ablation catheter for septal reduction therapy having a cooling effect, and more particularly, to a RF ablation catheter for septal reduction therapy that is for performing RF ablation, in which RF energy is applied to an interventricular septum, for septal reduction therapy such as therapy for hypertrophic cardiomyopathy, which is a disease in which an interventricular septum of the left ventricle of the heart of the animal or human body thickens, therapy that requires reduction of an interventricular septum, or therapy for ventricular tachycardia.

Also, the present disclosure relates to a RF ablation catheter for septal reduction therapy having a cooling effect that is for preventing carbonization of a tissue of the body (interventricular septum) around an electrode.

2. Description of the Prior Art

Examples of septal reduction therapy include therapy for hypertrophic cardiomyopathy, therapy that requires reduction of an interventricular septum, or therapy for ventricular tachycardia.

Among the examples of septal reduction therapy, the therapy for hypertrophic cardiomyopathy is therapy for a heart disease in which the wall of the left ventricle thickens without other symptoms such as aortic valvular stenosis or high blood pressure that may cause left ventricular hypertrophy. Hypertrophic cardiomyopathy is found in 1 out of every 500 people of the entire population, and various types of left ventricular hypertrophy are observed. The most common and typical features of left ventricular hypertrophy are asymmetrical septal hypertrophy and variable obstruction (blockage due to closure) of the left ventricular outflow tract.

Figure 1:
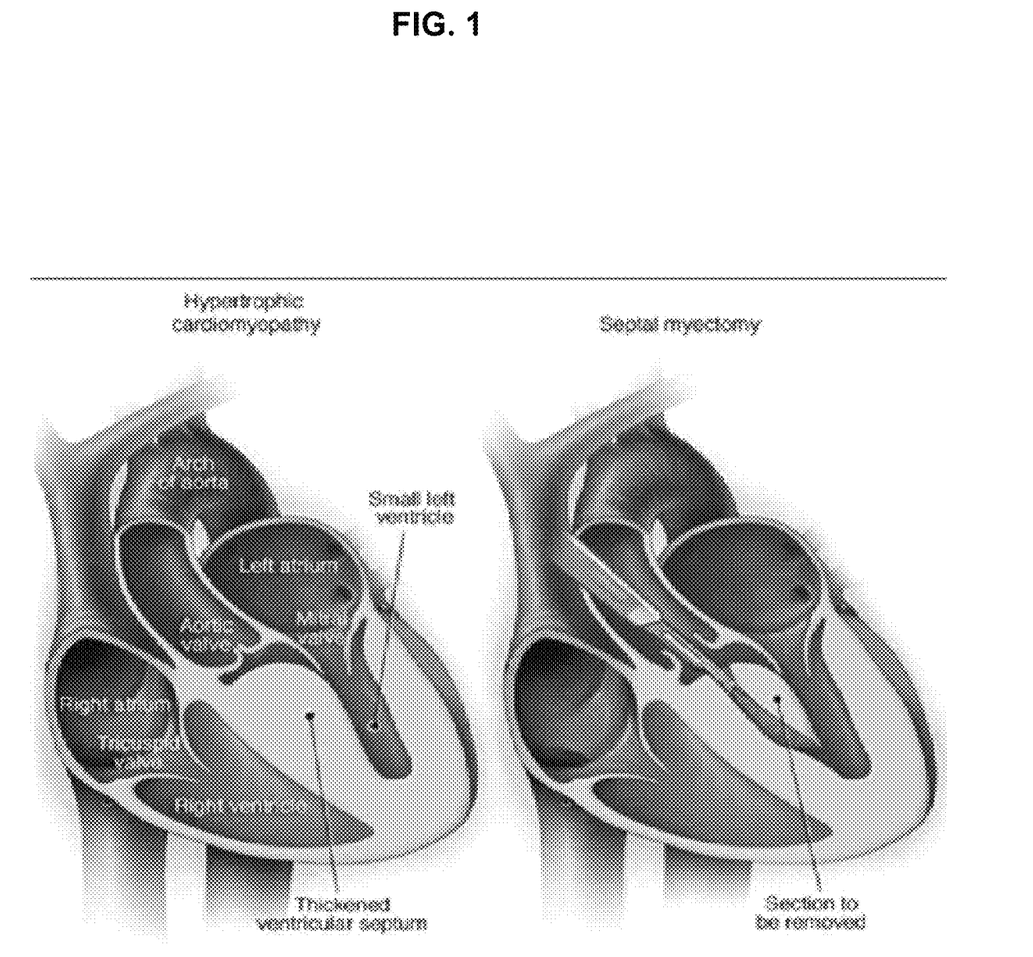
FIG. 1 illustrates symptoms of hypertrophic cardiomyopathy and a surgical method.

FIG. 1 is a view illustrating symptoms of hypertrophic cardiomyopathy and a surgical method that is commonly performed nowadays.

Referring to FIG. 1, a common method of surgery for hypertrophic cardiomyopathy is a method in which a knife is inserted into a left ventricle through an aortic valve and then a hypertrophied interventricular septum of the left ventricle is removed as illustrated. That is, a method in which a skilled specialist uses a knife to remove a hypertrophied interventricular septum is used.

Meanwhile, as another method, a method using RF energy has been presented in recent years. Methods of treatment for septal hypertrophy through RF ablation have been presented from time to time in the past, but all of the methods are methods in which a catheter is placed in a left ventricle and RF ablation is performed on a surface of the left ventricle.

In recent years, a technique in which a needle is used to penetrate the inside, instead of a surface, of a site of septal hypertrophy to treat septal hypertrophy has been presented, and the technique has been reported as being surprisingly highly effective in treating septal hypertrophy. That is, in recent years, it has been presented that performing RF ablation by accessing the inside of the interventricular septum (intra-septum) is highly effective in treating septal hypertrophy.

(Percutaneous Intramyocardial Septal Radiofrequency Ablation for Hypertrophic Obstructive Cardiomyopathy. Journal of the American College of Cardiology Volume 72, Issue 16, October 2018)

However, therapy according to the above paper has a disadvantage in that, since a hard needle is used to access the inside of the interventricular septum (intra-septum), the therapy is very dangerous.

Additional examples of prior art include Korean Patent Registration No. 10-1626958 (Date of Registration: May 27, 2016) (Title of Invention: RF catheter with Multi-electrode); and Percutaneous Intramyocardial Septal Radiofrequency Ablation for Hypertrophic Obstructive Cardiomyopathy. Journal of the American College of Cardiology Volume 72 (Date of presentation: Oct. 16, 2018).

SUMMARY OF THE INVENTION

The present disclosure is directed to providing a RF ablation catheter for septal reduction therapy that, by injecting a cooling saline solution (a coolant) from a proximal part of the catheter to lower the temperature of an electrode of a distal part and prevent carbonization around the electrode, facilitates RF transmission and widens a range of cauterization.

The present disclosure is also directed to providing a RF ablation catheter for septal reduction therapy that is capable of allowing reduction of an outer diameter of the RF catheter, that is capable of easily and smoothly passing through narrow blood vessels in the heart, that is capable of minimizing the possibility of contact with a RF power wire, a temperature sensor wire, and the like and thus reducing the occurrence of insulation-related problems which may occur in the catheter, and that is capable of allowing a length of a tube, through which a coolant is delivered, to be short so that the coolant is able to be injected using a pump having a lower pressure.

The objectives of the present disclosure are not limited to those mentioned above, and other unmentioned objectives should be clearly understood by those of ordinary skill in the art to which the present disclosure pertains from the following description.

An exemplary embodiment of the present disclosure provides a RF catheter for septal reduction therapy, the RF catheter including: an intra-septal part in which a tapered tip which becomes thinner toward an end thereof is formed at an end of a distal part so as to penetrate an interventricular septum and be inserted thereinto and in which one or more electrodes are formed at positions on an outer circumferential surface that are adjacent to the tip; and a body part which is made of a soft material and has a guidewire lumen which passes through the intra-septal part from the center of the end of the tip to allow a guidewire to be inserted, a coolant inlet lumen which is connected from a proximal part to an inner portion of the intra-septal part to allow a coolant to be injected from the outside and which has an open end, and a coolant outlet lumen which communicates with the coolant inlet lumen and has an exit formed in a side surface.

The intra-septal part may penetrate the myocardium and be inserted thereinto with guidance of the guidewire, and the guidewire lumen and the coolant inlet lumen may not communicate with each other and may be partitioned from each other.

According to an exemplary embodiment of the present disclosure, the coolant introduced into the intra-septal part from the proximal part through the coolant inlet lumen may exit through the coolant outlet lumen and then be discharged into a coronary sinus or vein through the exit formed in the side surface of the body part.

According to an exemplary embodiment of the present disclosure, the coolant outlet lumen may have a structure that surrounds the coolant inlet lumen, and the coolant injected along the coolant inlet lumen may flow backward along the coolant outlet lumen surrounding the coolant inlet lumen and may be discharged into the coronary sinus or vein through the exit communicating with the coolant outlet lumen.

According to an exemplary embodiment of the present disclosure, the coolant outlet lumen may have a structure that surrounds the guidewire lumen, and the guidewire lumen may pass through the coolant outlet lumen.

According to another exemplary embodiment of the present disclosure, the guidewire lumen may be disposed adjacent to the coolant outlet lumen instead of passing through the coolant outlet lumen.

According to an exemplary embodiment of the present disclosure, the electrode may be connected to a RF generator and serve to receive RF energy and emit the RF energy and may serve to sense an electrical signal of a myocardium or apply electrical stimulation thereto.

According to an exemplary embodiment of the present disclosure, the guidewire lumen may come in close contact with the guidewire passing therethrough, and a gap may not be present therebetween.

According to an exemplary embodiment of the present disclosure, a spiral coil wire or a braided wire may be formed in the intra-septal part, and the wire may be insulated from the electrode.

According to an exemplary embodiment of the present disclosure, in the intra-septal part, a hydrophilic polymer coating layer may be formed on a surface portion excluding a surface of the electrode.

According to an exemplary embodiment of the present disclosure, the tapered tip may have a length in a range of 5 to 20 mm, a sharp end of the tapered tip may have a thickness in a range of 1.2 to 1.4 Fr, and the opposite side of the sharp end may have a thickness in a range of 3 to 6 Fr.

According to an exemplary embodiment of the present disclosure, an electrode wire configured to transmit RF energy to the electrode may be covered with a sheath and spirally wrapped around a surface of the catheter, and as many electrode wires as the number of electrodes may be connected. Preferably, the electrode wire may be a silver wire.

According to an exemplary embodiment of the present disclosure, in order to measure the temperature of the electrode, two strands of a thermocouple wire may be spirally wrapped around the surface of the catheter from the proximal part to the distal part while being wound together. More preferably, one strand of the thermocouple wire may be a nickel-chromium wire that is harmless to the human body, and the other strand of the thermocouple wire may be a nickel-alumel wire that is harmless to the human body.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

The advantages, features, and methods of achieving the same of the present disclosure will become more apparent by referring to embodiments described in detail below with reference to the accompanying drawings. However, the present disclosure is not limited to the embodiments disclosed below and may be implemented in various different forms. The present embodiments make the disclosure of the present disclosure complete and are provided to completely inform those of ordinary skill in the art to which the present disclosure pertains of the scope of the present disclosure. The present disclosure is only defined by the scope of the claims.

An important aspect of the present disclosure is a therapy method in which a soft catheter-type RF ablation catheter is provided instead of a hard needle and the RF ablation catheter is used to intra-myocardially or intraseptally obtain a therapeutic effect of septal reduction therapy. That is, the present disclosure proposes a method for penetrating into a tissue using a soft catheter instead of a hard needle.

Figure 2:
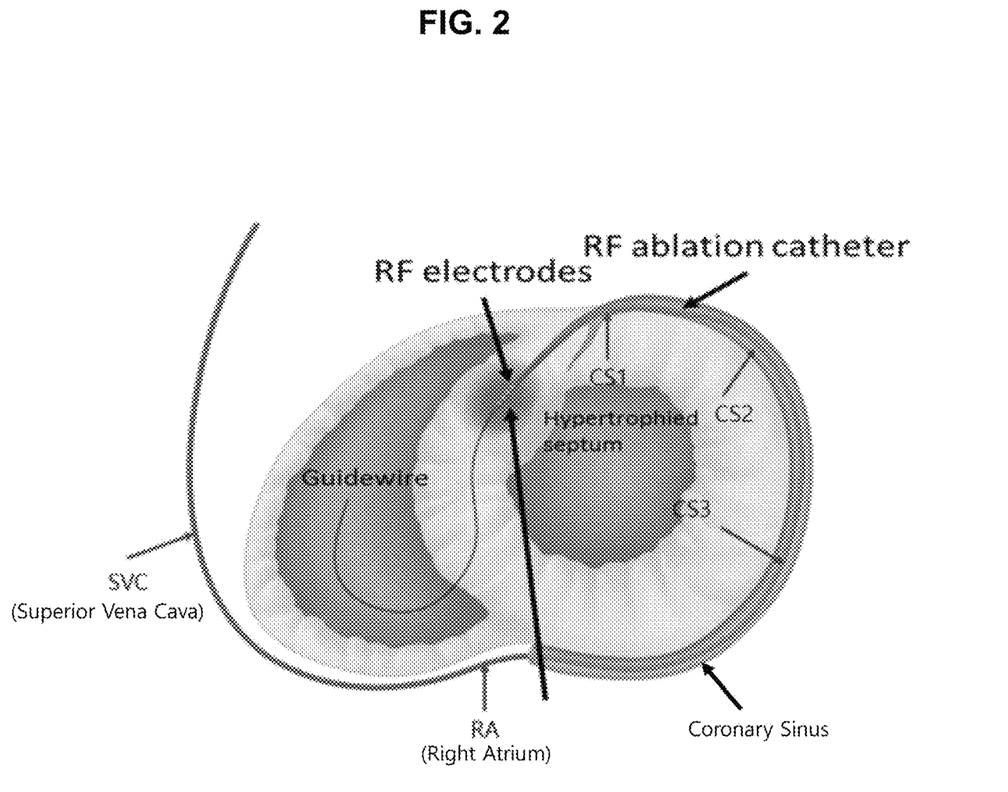
FIG. 2 is a schematic diagram illustrating a RF ablation catheter for septal reduction therapy of the present disclosure and a therapy method using the same.

FIG. 2 is a schematic diagram illustrating a RF ablation catheter for septal reduction therapy of the present disclosure and a therapy method using the same.

Referring to FIG. 2, according to the present disclosure, a guidewire is placed in a hypertrophied interventricular septum through a coronary sinus and a septal vein, and then a RF ablation catheter is delivered to a treatment target site (that is, the hypertrophied interventricular septum) along the guidewire placed in advance. Then, in a state in which a coolant is continuously injected from the outside, a RF generator is used to apply RF energy to an electrode formed on an end of the RF ablation catheter to perform RF ablation.

Preferably, prior to performing RF ablation, an electrical signal of the myocardium may be sensed or electrical stimulation may be applied thereto using the electrode, and then, by checking an electrocardiogram of a cardiac rhythm that is generated according thereto, whether the electrode is disposed in the vicinity of (close to) the bundle of His may be determined.

First, a method of placing a guidewire 10 in a treatment target site (hypertrophied interventricular septum) will be described.

A very thin guidewire (having a diameter of around 0.014") is placed in a hypertrophied interventricular septum, which is a target site, via a coronary sinus and a septal vein.

In the present disclosure, in order to access the interventricular septum, which is a treatment target for septal reduction therapy, through the septal vein, the coronary sinus having an opening located in the right atrium is used. Access to the coronary sinus is made using a neck vein or a femoral vein or is made using a guiding catheter via the superior vena cava or the inferior vena cava.

As the guiding catheter, a balloon-tipped guiding catheter and/or a balloon-tipped dual lumen microcatheter is used. The guiding catheter is a catheter for guiding the guidewire to a desired position.

Upon accessing the coronary sinus, the guiding catheter is placed at the distal part of the coronary sinus, and a pressurized venogram is performed through the guiding catheter. A balloon-tipped guiding catheter is ideal for a pressurized venogram When a septal vein venogram is performed through the pressurized venogram, a percutaneous transluminal coronary angioplasty (PTCA) guidewire having a diameter of about 0.014" is inserted into a septal vein that is the closest to the target site. For the PTCA guidewire, imaging guidance in which real-time imaging equipment for an echocardiogram or the like is utilized to notify whether the wire reaches the target site enables more precise therapy. In order to more precisely guide the orientation of the PTCA guidewire, a dual lumen microcatheter may be used to precisely guide the wire to the target site.

That is, in order to place the guidewire in the interventricular septum through a septal vein, (1) a pressurized venogram with a balloon-tipped guiding catheter and/or (2) a dual lumen microcatheter may be used.

A pressurized venogram is used to make the septal vein more visible. To this end, a balloon-tipped guiding catheter may be used as an auxiliary means.

Also, a dual lumen microcatheter or the like may be used as an auxiliary means to place the guidewire in a desired direction in the interventricular septum. The dual lumen microcatheter is a catheter in which two lumens are formed to insert guidewires. A first guidewire is placed in the septal vein through a first lumen of the dual lumen microcatheter, and then a second guidewire is inserted through a second lumen of the dual lumen microcatheter. The second guidewire may be moved in a different direction from the first guidewire. In this way, the dual lumen microcatheter is an auxiliary catheter for therapy that is very useful in allowing a desired guidewire to reach a target site in the interventricular septum.

In a septal vein located in a tissue of the interventricular septum instead of a surface of the interventricular septum, free movement of a guidewire is possible without problems such as bleeding. Since the septal vein is present in the interventricular septum, a guidewire is placed inside the hypertrophied interventricular septum (intra-septum) using the septal vein. When the septal vein is used, the guidewire may also pass through the septal vein, deviate therefrom, and move to a desired place as necessary. Here, the dual lumen microcatheter which has been described above may be used.

Although a similar approach is theoretically possible even when a septal artery is used, since anatomical locations thereof vary, it is often difficult for a guidewire to reach a target site. In such a case, when the guidewire passes through and exits the septal artery, serious problems such as intramyocardial bleeding may be caused. Also, when therapy is performed using the septal artery, cases in which a thrombus or dissection occurs in the septal artery often occur, which is fatal. Therefore, as in the present disclosure, a guidewire is inserted using the septal vein.

The method of access through the septal vein according to the present disclosure may prevent therapeutic complications that are caused in methods in which access to a left ventricular (LV) endocardium occurs via a septal artery, an aortic valve, or a mitral valve or in which the access occurs due to direct needle puncture or the like.

Meanwhile, conventionally, treatment in which alcohol is injected into a septal artery has been performed. The treatment may also cause a problem such as an unnecessary myocardial infarction due to difficulty in controlling the distribution of alcohol and alcohol being delivered to an undesired part. The treatment is also prone to causing a conduction system disorder.

Next, along the guidewire placed in the hypertrophied interventricular septum, the RF ablation catheter is placed at the target site (the inside of the hypertrophied interventricular septum). That is, after one or more guidewires are placed at the target site, the RF ablation catheter is inserted along the guidewires so that the electrode reaches the target site.

In a state in which the electrode of the RF ablation catheter is placed at the target site (the inside of the hypertrophied interventricular septum), while a coolant (saline solution) is injected from the outside through a coolant outlet lumen in the RF ablation catheter, a RF generator is used to apply RF energy to a RF electrode formed on an end of the RF ablation catheter to perform RF ablation.

Preferably, prior to performing RF ablation, determining whether the electrode is disposed in the vicinity of the bundle of His is performed. The determining of whether the electrode is disposed in the vicinity of the bundle of His is possible by directly sensing an electrical signal of the myocardium or checking an electrocardiogram of a cardiac rhythm that is generated at the time of electrical stimulation.

Referring to FIG. 2, the RF ablation catheter of the present disclosure passes through the right atrium (RA) via the superior vena cava (SVC) or the inferior vena cava (IVC), passes through the coronary sinus (CS), and then penetrates the interventricular septum and is inserted thereinto. In this state, RF energy is supplied to the electrode to perform ablation. In the RF ablation catheter of the present disclosure, a coolant injected from a proximal part exits through the coolant outlet lumen and is discharged through an exit of the coolant outlet lumen that is formed in a side surface of a body part. Since the exit is located in the CS, RA, or SVC (or IVC), the coolant flows into the CS, RA, or vein.

Referring to FIG. 2, the exit of the coolant outlet lumen through which the coolant is discharged is located at CS1, CS2, CS3, RA, or SVC that is indicated by a red arrow. Here, CS1, CS2, CS3, RA, and SVC only refer to approximate locations where the exit may be located and do not necessarily refer to accurate locations. That is, the exit through which the coolant is discharged may be located at any point between the CS, RA, and SVC (or IVC).

Figure 3:
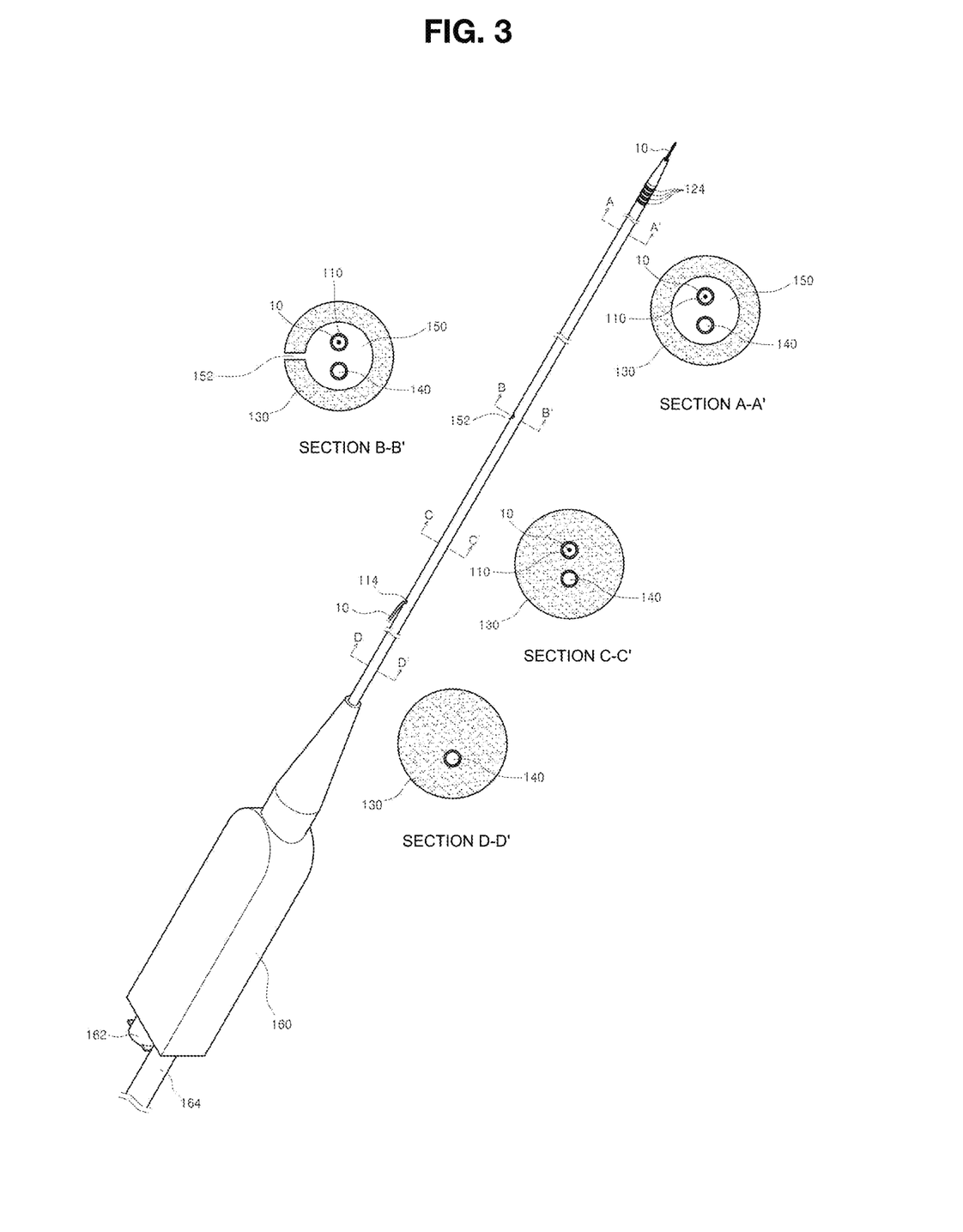
FIG. 3 illustrates an overall perspective view of the RF ablation catheter for septal reduction therapy and illustrates enlarged cross-sectional views of portions of the RF ablation catheter according to an embodiment of the present disclosure.
Figure 4:
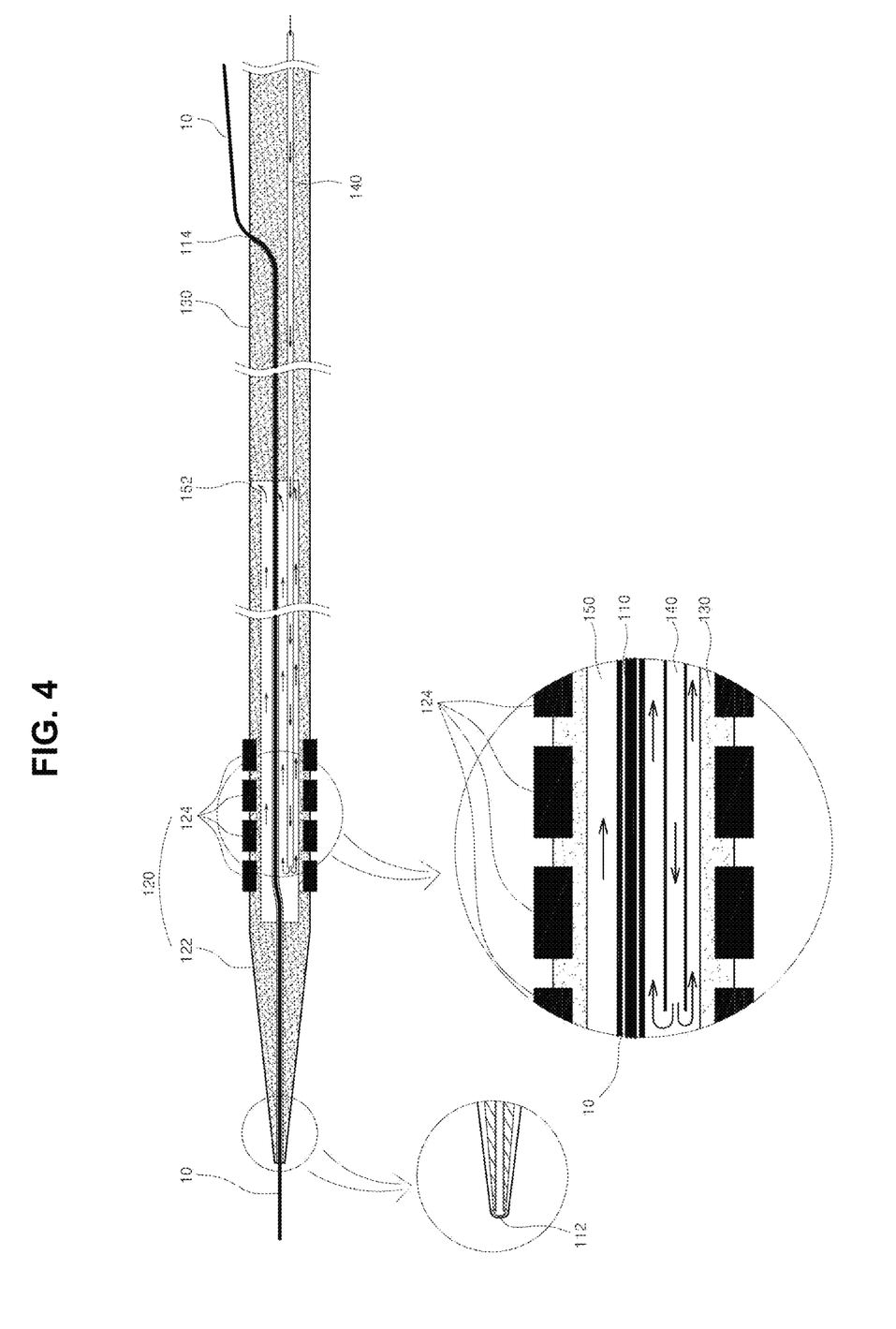
FIG. 4 illustrates a cross-sectional view of the RF ablation catheter for septal reduction therapy and illustrates enlarged cross-sectional views of portions of the RF ablation catheter according to an embodiment of the present disclosure.

FIG. 3 illustrates an overall perspective view of the RF ablation catheter for septal reduction therapy and illustrates enlarged cross-sectional views of portions of the RF ablation catheter according to an embodiment of the present disclosure, and FIG. 4 illustrates a cross-sectional view of the RF ablation catheter for septal reduction therapy and illustrates enlarged cross-sectional views of portions of the RF ablation catheter according to an embodiment of the present disclosure.

Referring to FIGS. 3 and 4, a RF ablation catheter 100 is mainly divided into a body part 130 and an intra-septal part 120.

The intra-septal part 120 is a portion formed at a distal part of the body part 130 and is a portion inserted into the interventricular septum. The intra-septal part 120 has a thickness of around 3 to 6 Fr (preferably, about 4 Fr) which is a size that does not cause much damage to the interventricular septum when the intra-septal part 120 is inserted into the interventricular septum.

The intra-septal part 120 includes one or more electrodes 124 formed on a surface and a tapered tip (or a tissue penetrating tip) 122 which becomes thinner toward an end to penetrate and enter the interventricular septum along a guidewire.

Preferably, the tapered tip 122 has a length in a range of about 5 to 20 mm (preferably, about 10 mm), and a sharp end of the tapered tip 122 has a thickness in a range of about 1.2 to 1.4 Fr. The opposite side of the sharp end has the same thickness as an outer shape of the intra-septal part (preferably, a thickness in a range of 3 to 6 Fr, and more preferably, a thickness in a range of 4 to 5 Fr). The tapered tip 122 has a very long, thin shape in which the length is five times to twenty times greater than the thickness of the opposite side of the sharp end (that is, the thickness of the outer shape of the intera-septal part).

The RF ablation catheter 100 has a guidewire lumen into which a guidewire is inserted formed therein so that the RF ablation catheter 100 may be inserted into the interventricular septum along the guidewire located in the interventricular septum. An inlet 112 of a guidewire lumen 110 is formed in the sharp end of the intra-septal part.

Preferably, the guidewire and the inlet 112 of the guidewire lumen should come in close contact with each other, and a gap should not be present therebetween. That is, the guidewire and the end of the tip should have a high-precision structure in which mismatch is not present therebetween.

The reason why there should not be a gap between the inlet of the guidewire lumen and the guidewire is that when the tip enters the ventricular septum, resistance should be minimized so that the tissue of the interventricular septum is not damaged. This is because, in the present disclosure, the tapered tip 122 has to penetrate and enter the tissue of the interventricular septum while functioning like a needle. In a case in which a gap is formed between the inlet of the guidewire lumen and the guidewire, when the tapered tip is inserted into the interventricular septum, the tip is resisted by the tissue of the interventricular septum, thus causing a problem in that the tissue of the interventricular septum may be damaged.

Since the RF ablation catheter should be inserted into the interventricular septum along the guidewire, of course, the RF ablation catheter should be able to move along the guidewire through the guidewire lumen even when the inlet of the guidewire lumen and the guidewire are in close contact.

One or more electrodes are formed in the intra-septal part. The electrode not only serves to sense an electrical signal of the myocardium or apply electrical stimulation thereto but also serves to transmit RF energy of the RF generator.

The electrode is connected to an electrode wire (illustrated in FIGS. 5 and 6), and the electrode wire is connected to the proximal part along the inside or an outer surface of the catheter, exits the catheter, and is connected to an external connector. Depending on where the external connector is connected, the electrode may perform various functions such as electrical signal sensing and pacing as well as RF emission.

In order to determine whether the electrode is disposed in the vicinity of the bundle of His (that is, in order to identify the location of the conduction system), the electrode is used for the purpose of directly sensing an electrical signal of the myocardium or applying electrical stimulation to the myocardium (pacing the myocardium). Also, in order to perform RF ablation, the electrode is used for the purpose of transmitting RF energy of the RF generator. That is, the electrode may be used for various purposes such as the purpose of determining whether the electrode is disposed in the vicinity of the bundle of His and the purpose of transmitting RF energy.

First, in a case in which the electrode is used for the purpose of determining whether the electrode is disposed in the vicinity of the bundle of His, the electrode is used for the purpose of directly sensing an electrical signal of the myocardium or applying electrical stimulation thereto. In a case in which the electrode applies electrical stimulation to the myocardium, by checking an electrocardiogram of a cardiac rhythm that is generated due to the electrical stimulation, the location of the conduction system such as the bundle of His may be indirectly identified.

The RF ablation catheter may easily access the interventricular septum, but there is a risk that the RF ablation catheter may be located close to the bundle of His. When RF ablation is performed in a state in which the electrode of the RF ablation catheter is in the vicinity of the bundle of His, there is a risk that the conduction system of the heart is destroyed due to RF ablation being performed on the conduction system of the heart.

In order to prevent such a risk, in the present disclosure, the location of the conduction system such as the bundle of His should be identified through the electrode prior to performing RF ablation. To this end, the electrode serves to perform sensing or pacing. An electrical signal of the myocardium may be directly sensed using the electrode to identify the location of the conduction system, or electrical stimulation may be applied to the myocardium using the electrode to indirectly identify the location of the conduction system such as the bundle of His through an electrocardiogram of a cardiac rhythm that is generated due to the electrical stimulation.

In a case in which the electrode is disposed in the vicinity of the bundle of His, the position of the RF ablation catheter should be changed to another position.

Only in a case in which the position of the electrode is sufficiently deviated from the bundle of His, is the external connector which is connected to the electrode connected to the RF generator, and RF energy is applied to perform RF ablation.

When performing RF ablation, the connector connected to the electrode is connected to the RF generator. The RF energy of the RF generator is transmitted to the electrode to perform RF ablation.

In a case in which a plurality of electrodes are formed, some electrodes may be used for the purpose of RF ablation, and the remaining electrodes may be used for the purpose of sensing or pacing. That is, the plurality of electrodes may be differentiated according to purpose, and the plurality of electrodes being used may be classified into electrodes used for the purpose of RF ablation and electrodes used for the purpose of sensing or pacing.

In another case, instead of differentiating the electrodes according to the two purposes, the electrodes may be used for both the purpose of sensing or pacing and the purpose of RF ablation. That is, the electrodes may be used for the purpose of sensing or pacing first, and then, the connector connected to the electrodes may be connected to the RF generator to use the electrodes for applying RF energy.

In the present disclosure, the proximal part of the catheter refers to one side end of the catheter that exits the human body, and the distal part of the catheter refers to the other side end of the catheter that is inserted into the human body.

Although not illustrated, preferably, the intra-septal part 120 has a spiral coil wire or a braided wire, which is insulated, formed therein. This is to prevent kinking of the intra-septal part and improve pushability and trackability when the intra-septal part is inserted into the interventricular septum. Pushability is often understood as the ability to transmit a force from the proximal part of the catheter to the distal part of the catheter while minimizing or eliminating kinking. Trackability is often understood as the ability to navigate the cathether through tortuous vasculature. Of course, both the spiral coil wire and the braided wire should be insulated from the electrode or the electrode wire.

Preferably, the intra-septal part may have a hydrophilic polymer coating layer formed on a surface. This is to allow the intra-septal part to more easily move into the tissue of the interventricular septum. The hydrophilic polymer coating layer is harder than the catheter made of a soft material and thus may facilitate insertion of the intra-septal part into the tissue of the interventricular septum. Since the electrode should be exposed to the surface, the hydrophilic polymer coating layer is not formed on the portion where the electrode is formed.

The body part 130 is a portion constituting the body of the catheter. The body part 130 has an outer diameter that is greater than or equal to the outer diameter of the intra-septal part 120. In order to prevent kinking of the catheter when the intra-septal part is pushed into the interventricular septum, the body part 130 should have sufficient stiffness to efficiently push in the intra-septal part.

Preferably, like the intra-septal part, the body part may have a spiral coil wire or a braided wire, which is insulated, formed therein. In this way, kinking of the catheter may be prevented, and pushability and trackability may be improved.

Meanwhile, when RF energy is applied using the RF ablation catheter, when the temperature rises excessively, in addition to the formation of char (black dots) on the interventricular septum, tissue defects may appear in the myocardium. Also, the gas produced by the sudden burning of the tissue causes a sudden increase in the intra-tissue pressure, resulting in barotrauma, which can lead to a risk of perforation of the heart.

At the time of RF ablation, a coolant (saline solution) should be used to cool a site on which RF ablation will be performed. To perform cooling, a coolant should be injected into the RF ablation catheter.

The coolant injected from the proximal part may, after cooling down the temperature of the electrode of the intra-septal part, return to the proximal part or be discharged through the side surface of the body part.

FIG. 3 illustrates an overall perspective view of the RF ablation catheter for septal reduction therapy and illustrates enlarged cross-sectional views of portions of the RF ablation catheter according to an embodiment of the present disclosure. FIG. 4 illustrates a cross-sectional view of the RF ablation catheter for septal reduction therapy and illustrates enlarged cross-sectional views of portions of the RF ablation catheter according to an embodiment of the present disclosure.

Referring to FIGS. 3 and 4, in the RF ablation catheter illustrated in FIGS. 3 and 4, a coolant (saline solution) is injected from the proximal part through a coolant inlet lumen 140, enters the intra-septal part 120 on which the electrode 124 is disposed, exits through a coolant outlet lumen 150 and flows backward along the coolant outlet lumen, and then is discharged through an exit 152 of the coolant outlet lumen 150 that is formed in the side surface of the body part 130.

In a case in which septal reduction therapy is performed using the RF ablation catheter of the present disclosure, when the RF catheter is inserted along the guidewire, the tapered tip 122 at the distal part of the RF catheter penetrates and enters the interventricular septum (myocardium) and is inserted into the interventricular septum. Here, since the exit 152 of the coolant outlet lumen 150, which is formed in the side surface of the body part 130, is located in the CS, RA, or vein, the coolant being discharged is discharged into the CS, RA, or vein. The guidewire lumen 110 is a lumen through which the guidewire is inserted and is an essential element for inserting the RF catheter into a target site (interventricular septum) along the guidewire. The guidewire lumen 110 passes through the intra-septal part 120 from the inlet 112 formed at the center of the end of the tapered tip and has an outlet 114 formed in the side surface of the body part.

The outlet 114 of the guidewire lumen 110 may be formed at various positions such as a proximal part, an intermediate part, or a distal part of the body part. Preferably, as illustrated in FIGS. 3 and 4, the outlet 114 of the guidewire lumen is formed at the proximal part of the body part. This is to allow the guidewire to be disposed in the RF catheter while the guidewire and the catheter are prevented from being separated from each other as much as possible so that the RF catheter may be easily inserted along the guidewire.

The guidewire lumen 110 is partitioned from the coolant outlet lumen 150 without communicating therewith. That is, the guidewire lumen 110 and the coolant outlet lumen 150 are separated and divided from each other. This is to ensure that the guidewire moving along the guidewire lumen is not obstructed by the coolant flowing through the coolant outlet lumen.

Preferably, the coolant outlet lumen has a structure surrounding the guidewire lumen, that is, a structure in which the guidewire lumen is disposed.

The coolant inlet lumen 140 is a path for injecting a coolant into the RF catheter. To allow the coolant to be injected from the outside, the coolant inlet lumen 140 is connected from the proximal part to the inside of the intra-septal part, and an end of the coolant inlet lumen 140 is open. Therefore, the coolant introduced from the outside is injected to the inside of the intra-septal part.

The coolant inlet lumen and the coolant outlet lumen communicate with each other. More preferably, in the vicinity of the intra-septal part (at the distal part), the coolant outlet lumen has a structure surrounding the coolant inlet lumen, that is, a structure in which the coolant inlet lumen is disposed.

The coolant injected from the proximal part through the coolant inlet lumen 140 flows through the coolant inlet lumen, exits the coolant inlet lumen due to the open end of the coolant inlet lumen, and flows along the inside of the coolant outlet lumen surrounding the coolant inlet lumen.

Since the RF electrode is disposed on the outer surface of the intra-septal part and the end of the coolant inlet lumen is connected to the inside of the intra-septal part, the coolant may be injected up to the intra-septal part and cool the electrode and the catheter. Meanwhile, since the end of the coolant outlet lumen is blocked, the coolant flows backward along the coolant outlet lumen and then is discharged to the outside through the exit 152 formed in the side surface of the body part.

A typical conventional catheter that is cooled by a coolant (saline solution) has a structure in which a coolant inlet lumen and a coolant outlet lumen are connected from the proximal part to the distal part of the catheter.

However, in the present disclosure, instead of the coolant outlet lumen being connected to the proximal part of the catheter, the exit of the coolant outlet lumen is formed in the side surface of the body part so that the coolant is discharged into the CS, RA, SVC (or IVC), and the coolant outlet lumen has a structure surrounding the coolant inlet lumen.

Accordingly, the catheter of the present disclosure has an advantage in that, since it is not necessary to form a separate coolant outlet tube to the proximal part, the outer diameter of the catheter may be reduced. In particular, for the RF ablation catheter for septal reduction therapy that aims to reach the interventricular septum via narrow blood vessels in the heart, reducing the outer diameter of the catheter is very important.

Also, the catheter of the present disclosure has advantages in that, since the possibility of contact with a RF power wire, a temperature sensor wire, and the like is minimized, the occurrence of insulation-related problems which may occur in the catheter may be reduced, and due to a length of a tube, through which a saline solution (coolant) is delivered, being shortened, the saline solution may be injected using a pump having a lower pressure.

Meanwhile, according to the manner of applying potential during RF ablation, there are mainly a method using a monopolar mode RF ablation catheter and a method using a bipolar mode RF ablation catheter.

The monopolar mode RF ablation catheter is a catheter in which the same polarity is applied to all the electrodes of the RF ablation catheter, and the bipolar mode RF ablation catheter is a catheter in which different polarities are applied to the electrodes of the catheter.

In a case in which the bipolar mode RF ablation catheter is used, a separate grounding device is not necessary, but in a case in which the monopolar mode RF ablation catheter is used, a separate grounding device is necessary.

The case in which the monopolar mode RF ablation catheter is used includes a case in which the grounding device is placed in a part of the human body other than the interventricular septum and a case in which the grounding device is placed in the interventricular septum.

The case in which the grounding device is placed in a part of the human body other than the interventricular septum is a method in which the RF ablation catheter is placed in the interventricular septum, a ground plate (grounding device) is grounded on another part of the human body (a human body part such as the back, a buttock, or a calf), and then RF energy is applied to the electrode of the RF ablation catheter to perform RF ablation.

The case in which the grounding device is placed in the interventricular septum is a method in which the RF ablation catheter is placed in the interventricular septum, the grounding device, which performs grounding, is placed around the electrode of the RF ablation catheter, and then RF energy is applied to the electrode of the RF ablation catheter to perform RF ablation.

Although FIGS. 3 and 4 illustrate a state in which a plurality of electrodes are formed, only one electrode may be formed for RF ablation, which corresponds to the monopolar mode. In the case in which a single electrode is formed on the intra-septal part, the electrode may have a wide width that corresponds to the sum of the widths of three to four electrodes illustrated in FIG. 3.

Meanwhile, the guidewire lumen may be formed inside the coolant outlet lumen as illustrated in FIGS. 3 and 4, but the present disclosure is not necessarily limited thereto.

The guidewire lumen may also be disposed adjacent to the coolant outlet lumen instead of passing through the coolant outlet lumen. That is, the guidewire lumen may be separately formed from the coolant outlet lumen instead of passing through the coolant outlet lumen. In this case, despite the decrease in the diameter of the coolant outlet lumen, the coolant outlet lumen has a more stable structure because horizontal movement of the guidewire lumen does not occur in the coolant outlet lumen.

Figure 5:
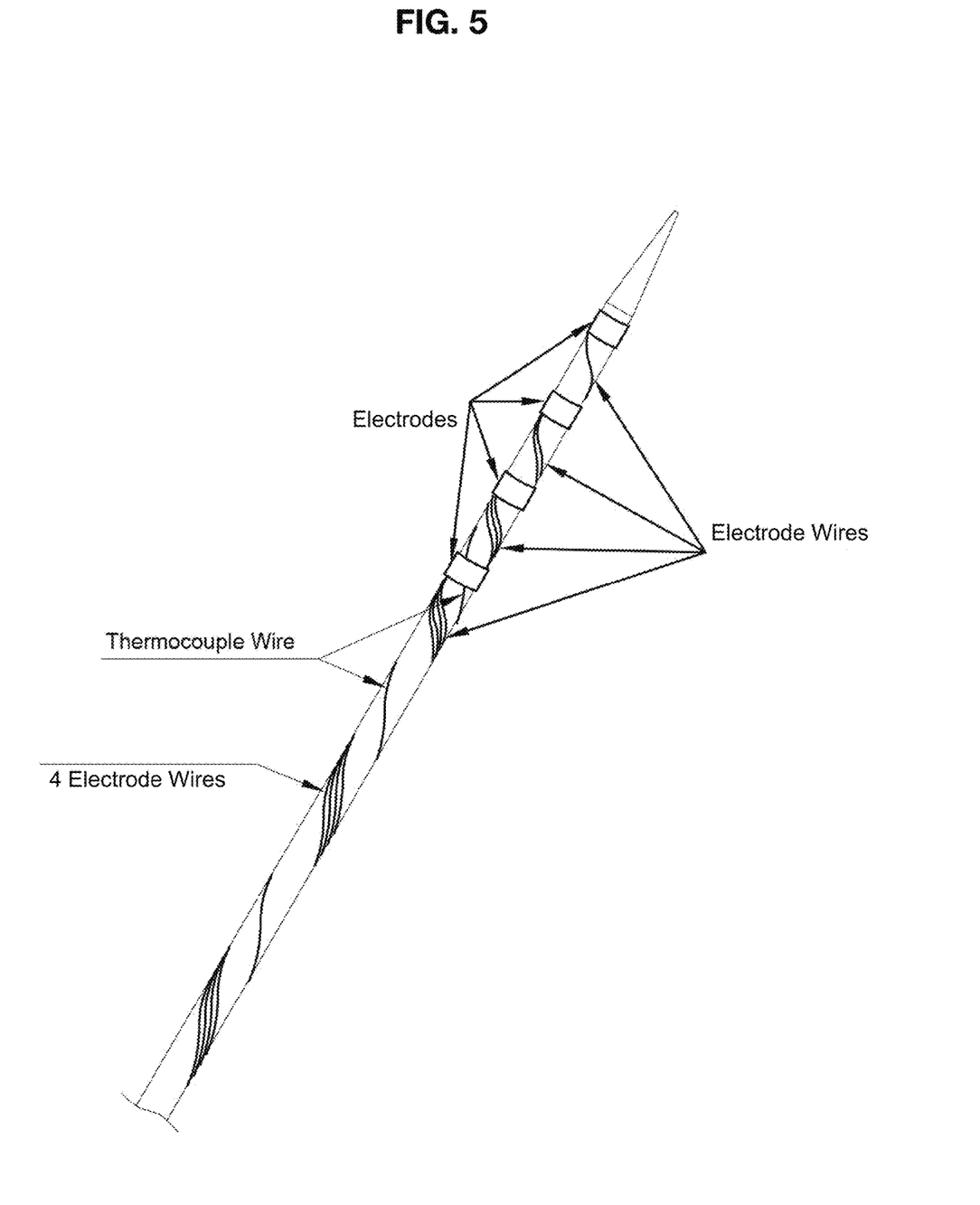
FIG. 5 illustrates the shapes of electrode wires formed on a surface of the RF ablation catheter for septal reduction therapy and illustrates the catheter according to an embodiment of the present disclosure.

FIG. 5 illustrates the shapes of electrode wires formed on a surface of the RF ablation catheter for septal reduction therapy and illustrates the catheter according to an embodiment of the present disclosure.

The RF ablation catheter for septal reduction therapy that is illustrated in FIG. 5 has a structure having four electrodes. Preferably, a width of each electrode is in a range of about 1 mm to 10 mm. Each of the four electrodes is connected to one electrode wire, and a thermocouple wire for measuring a temperature of the distal part of the catheter is connected. The electrode wires and the thermocouple wire are connected at the proximal part of the catheter. Each of the four electrodes has a width of about 1 mm, but the width of each electrode is not necessarily limited thereto and, of course, may be appropriately adjusted according to the number of electrodes. Electrodes with a larger width may be used in a case in which the number of electrodes is small, and electrodes with a smaller width may be used in a case in which the number of electrodes is large. Also, electrodes with different widths may be used in a single catheter.

RF energy supplied to the electrode is supplied through a silver wire that is spirally wrapped around a surface of the catheter. That is, RF energy for performing RF ablation is supplied to the electrode 124 through an electrode wire that is spirally wrapped around a surface of the catheter made of a soft plastic material.

The electrode wire is a wire configured to supply RF energy. Preferably, a silver wire is used as the electrode wire. The silver wire is insulated (covered) with a plastic material that is harmless to the human body. The RF ablation catheter of the present disclosure is inserted into the human body (CS, RA, or vein). Since the electrode wire has a structure surrounding the surface of the catheter, in a case in which the sheath of the electrode wire comes off when the catheter is inserted into the CS, RA, or vein, the electrode wire comes in contact with a tissue. Thus, materials such as copper that are harmful to the human body cannot be used. Therefore, in the present disclosure, a silver wire harmless to the human body is used as the electrode wire.

In the present disclosure, by using the silver wire as the electrode wire that transmits RF energy and spirally forming the silver wire around the surface of the catheter, it is possible to obtain advantages in that linearity of the catheter is improved and pushability thereof is improved.

Meanwhile, as illustrated in FIG. 5, in addition to the silver wire which is the electrode wire, a thermocouple wire is spirally wrapped around the surface of the catheter while being spaced apart from the electrode wire. The thermocouple wire is also covered with a harmless plastic material.

The thermocouple wire is for measuring the temperature around the electrode. That is, the thermocouple wire is a wire used as a thermoelectric thermometer. The thermocouple wire has a form in which two wires covered with a sheath are wound together and is spirally wrapped around the surface of the catheter while being spaced apart from the electrode wire (silver wire). The thermocouple wire is entirely covered with the sheath except for ends of the two wires so that the two wires are connected to each other and used as a thermoelectric thermometer.

Various thermocouple wires are in use nowadays, but in the present disclosure, since the thermocouple wire has a form wrapped around the surface of the catheter inserted into the human body, nickel-chromium or nickel-alumel is used for the thermocouple wire so that it is harmless to the human body even when the sheath of the thermocouple wire comes off. That is, one strand of the thermocouple wire is a nickel-chromium wire harmless to the human body, and the other strand of the thermocouple wire is a nickel-alumel wire harmless to the human body.

Since the thermocouple wire of the present disclosure is also spirally wrapped around the surface of the catheter, it is possible to obtain advantages in that linearity of the catheter is improved and pushability thereof is improved.

As described above, the number of electrodes may be changed, and, of course, the number of electrode wires configured to supply power to the electrode may also be changed according to the number of electrodes.

Figure 6:
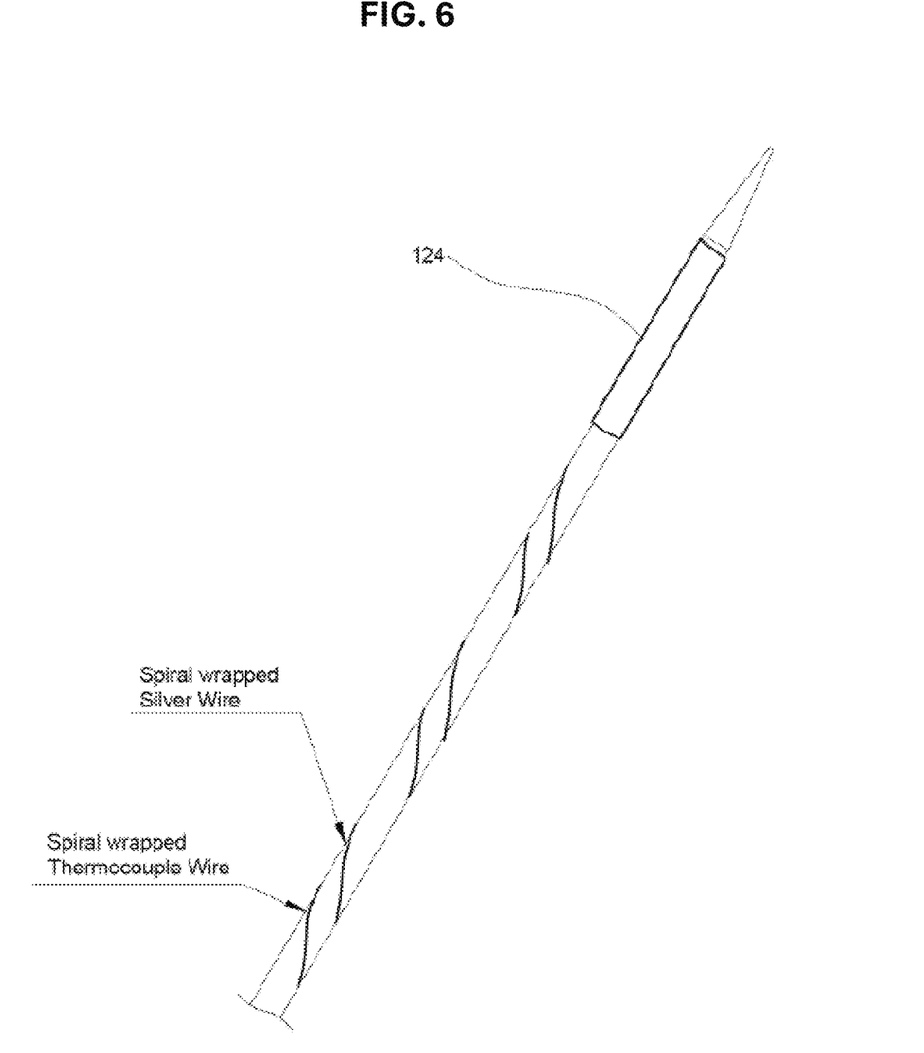
FIG. 6 illustrates the shapes of electrode wires formed on a surface of the RF ablation catheter for septal reduction therapy and illustrates the catheter according to another embodiment of the present disclosure.

FIG. 6 illustrates the shapes of electrode wires formed on a surface of the RF ablation catheter for septal reduction therapy and illustrates the catheter according to another embodiment of the present disclosure. FIG. 6 illustrates a case in which a single electrode is used.

Referring to FIG. 6, a single wide electrode 124 is formed in a form of being wrapped with a coil. Since the number of electrodes is one, the number of electrode wires formed to supply RF energy to the electrode is also one. The electrode wire is covered with a sheath and is spirally wrapped around the surface of the catheter. A silver wire may be used as the electrode wire so that it is harmless to the human body even when the sheath of the electrode wire comes off.

In addition to the electrode wire, a thermocouple wire for measuring the temperature of the distal part of the catheter is spirally wrapped around the surface of the catheter. The thermocouple wire is also covered with a sheath and has a structure in which two strands of wire are spirally wrapped around the surface of the catheter while being twisted and wound together. The structure and material of the thermocouple wire are the same as those described above.

As described above, in a state in which the electrode of the RF ablation catheter is placed in the interventricular septum, a coolant is injected into the RF ablation catheter to perform RF ablation. After a desired therapeutic effect is obtained by performing RF ablation, the device is entirely removed to complete the RF ablation for septal reduction therapy.

According to the present disclosure, there are the following advantageous effects.

1. Since RF ablation is performed using a soft RF ablation catheter instead of using a hard needle and the RF ablation catheter is able to smoothly enter along a septal vein which is curved, therapy can be safely performed.

2. Since the RF ablation catheter is able to pass through a coronary sinus and a septal vein, it is possible to prevent therapeutic complications that are caused in methods in which access to a left ventricular (LV) endocardium occurs via a septal artery, an aortic valve, or a mitral valve or in which the access occurs due to direct needle puncture or the like.

3. Preferably, cooling is performed when performing RF ablation. Through cooling, it is possible to reduce the risk of formation of char on the endocardium or the risk of tissue defects.

4. When RF energy is transmitted into the interventricular septum, (1) contact with surrounding tissues is good; (2) a homogeneous lesion, which is an advantage of RF energy, can be formed; and (3) since the extent of tissue defects can be controlled by stages by titrating a degree of RF, there is an advantage that a sufficient therapeutic effect can be expected even with a structure having a small diameter (in a range of about 2 to 6 Fr) that is able to pass through a ventricle.

5. At the same time, since it is possible to avoid tissue defects of the LV endocardium, complete atrioventricular block can be prevented, and since tissue defects uniformly occur, arrhythmogenecity can be minimized.

6. An electrode formed on a surface of the RF ablation catheter not only serves to apply RF energy but also serves to sense an electrical signal or apply an electrical stimulation.

Prior to performing RF ablation, an electrical signal of the myocardium may be directly sensed through an electrode or electrical stimulation may be applied to the myocardium through an electrode, and then, through an electrocardiogram of a cardiac rhythm that is generated according thereto, whether the electrode is disposed in the vicinity of the bundle of His may be determined in advance. In this way, stability of RF ablation can be improved, and accordingly, there is an advantage that reliability of the therapy of the present disclosure can be increased.

7. Since a coolant outlet lumen has a structure that surrounds a coolant inlet lumen, it is possible to reduce an outer diameter of the RF ablation catheter. In the case of the RF ablation catheter for septal reduction therapy that aims to reach the interventricular septum via narrow blood vessels in the heart, reducing the outer diameter of the catheter is very important.

8. Since the coolant outlet lumen has the structure surrounding the coolant inlet lumen and thus reduction of the outer diameter of the catheter is possible, there are advantages that, by minimizing the possibility of contact with a RF power wire, a temperature sensor wire, and the like, the occurrence of insulation-related problems which may occur in the catheter can be reduced, and due to a length of a tube, through which a saline solution (coolant) is delivered, being shortened, the saline solution can be injected using a pump having a lower pressure.

The embodiments of the present disclosure have been described above with reference to the accompanying drawings, but those of ordinary skill in the art to which the present disclosure pertains should understand that the present disclosure may be embodied in other specific forms without changing the technical spirit or essential features of the present disclosure. Therefore, the embodiments described above should be understood as being illustrative, instead of limiting, in all aspects.

What is claimed is:

1. A RF catheter for septal reduction therapy, the RF catheter comprising:

an intra-septal part in which a tapered tip which becomes thinner toward an end thereof is formed at an end of a distal part to penetrate an interventricular septum and be inserted thereinto and in which one or more electrodes are formed at positions on an outer circumferential surface that are adjacent to the tip; and a body part which is made of a soft material and has a guidewire lumen which passes through the intra-septal part from the center of the end of the tip to allow a guidewire to be inserted and has an outlet formed in a side surface of the body part, a coolant inlet lumen which is connected from a proximal part to an inner portion of the intra-septal part to allow a coolant to be injected from the outside and which has an open end, and a coolant outlet lumen which communicates with the coolant inlet lumen and has an exit formed in a side surface, wherein the intra-septal part penetrates the myocardium and inserted thereinto with guidance of the guidewire, and the coolant inlet lumen an open end, wherein the coolant outlet lumen has a structure surrounds the coolant inlet, wherein the guidewire lumen and the coolant inlet lumen do not communicate with each other and are partitioned from each other, wherein the guidewire lumen and the coolant outlet lumen do not communicate with each other and are partitioned from each other and the exit of the coolant outlet lumen is arranged to space apart from the outlet of the guidewire lumen;

wherein the coolant outlet lumen has a structure that surrounds the coolant inlet lumen, and the coolant injected along the coolant inlet lumen flows backward along the coolant outlet lumen surrounding the coolant inlet lumen and is discharged into the coronary sinus, right atrium, or vein through the exit communicating with the coolant outlet lumen wherein the coolant outlet lumen has a structure that surrounds the coolant inlet lumen, and the coolant injected along the coolant inlet lumen flows backward along the coolant outlet lumen surrounding the coolant inlet lumen and is discharged into the coronary sinus, right atrium, or vein through the exit communicating with the coolant outlet lumen.

2. The RF catheter of claim 1, wherein the coolant outlet lumen has a structure that surrounds the guidewire lumen, and the guidewire lumen passes through the coolant outlet lumen.

3. The RF catheter of claim 1, wherein the guidewire lumen is disposed adjacent to the coolant outlet lumen instead of passing through the coolant outlet lumen.

4. The RF catheter of claim 1, wherein the electrode is connected to a RF generator and serves to receive RF energy and emit the RF energy and serves to sense an electrical signal of the myocardium or apply electrical stimulation thereto.

5. The RF catheter of claim 1, wherein the guidewire lumen comes in close contact with the guidewire passing therethrough, and a gap is not present therebetween.

6. The RF catheter of claim 1, wherein a spiral coil wire or a braided wire is formed in the intra-septal part, and the wire is insulated from the electrode.

7. The RF catheter of claim 1, wherein, in the intra-septal part, a hydrophilic polymer coating layer is formed on a surface portion excluding a surface of the electrode.

8. The RF catheter of claim 1, wherein one end of the guidewire lumen is formed at the center of the end of the tapered tip, and the other end of the guidewire lumen is formed at a side surface of the catheter or an end of the proximal part of the catheter.

9. The RF catheter of claim 1, wherein the tapered tip has a length in a range of 5 to 20 mm, a sharp end of the tapered tip has a thickness in a range of 1.2 to 1.4 Fr, and the opposite side of the sharp end has a thickness in a range of 3 to 6 Fr.

10. The RF catheter of claim 1, wherein an electrode wire configured to transmit RF energy to the electrode is covered with a sheath and spirally wrapped around a surface of the catheter, and as many electrode wires as the number of electrodes are connected.

11. The RF catheter of claim 10, wherein the electrode wire is a silver wire.

12. The RF catheter of claim 1, wherein, in order to measure the temperature of the electrode, two strands of a thermocouple wire are spirally wrapped around the surface of the catheter from the proximal part to the distal part while being wound together.

13. The RF catheter of claim 12, wherein one strand of the thermocouple wire is a nickel-chromium wire that is harmless to the human body, and the other strand of the thermocouple wire is a nickel-alumel wire that is harmless to the human body.

* * * * *